(12) United States Patent
Shinoda

(10) Patent No.: US 7,904,259 B2
(45) Date of Patent: Mar. 8, 2011

(54) WATERPROOF TESTING DEVICE, WATERPROOF TESTING METHOD, AND WATERPROOF TEST PROGRAM

(75) Inventor: Takao Shinoda, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 43 days.

(21) Appl. No.: 12/339,992

(22) Filed: Dec. 19, 2008

(65) Prior Publication Data
US 2009/0164148 A1    Jun. 25, 2009

(30) Foreign Application Priority Data
Dec. 20, 2007  (JP) ................. 2007-329322

(51) Int. Cl.
*G01N 11/00*  (2006.01)
*G06F 19/00*  (2006.01)
(52) U.S. Cl. ......................................... 702/51
(58) Field of Classification Search ........... 702/51, 702/45, 50, 100, 113; 73/40, 40.7, 861
See application file for complete search history.

(56) References Cited

U.S. PATENT DOCUMENTS
2005/0199042 A1 * 9/2005 Perkins et al. ............. 73/40.7
2007/0089489 A1 * 4/2007 Lewnard et al. ............. 73/38

FOREIGN PATENT DOCUMENTS
JP    2003-165172 A    6/2003
JP    2005-226203    *   8/2005
* cited by examiner

*Primary Examiner* — Cindy H Khuu
(74) *Attorney, Agent, or Firm* — Fujitsu Patent Center

(57) ABSTRACT

A waterproof testing device tests waterproof performance of a waterproof component. The testing device includes an input unit, a storing unit and a determining unit. The input unit inputs permeability of one or more test objects with waterproof components disposed thereon and an air flow rate that is a volume of gas passing through the test object per unit time for each test object. The storing unit stores, in a data pair, the permeability and the air flow rate of each test object input by the input unit. The determining unit determines a range of permeability in which no water leakage occurs in the waterproof component based on a range of air flow rate in which no water leakage occurs and the stored permeability and air flow rate.

8 Claims, 6 Drawing Sheets

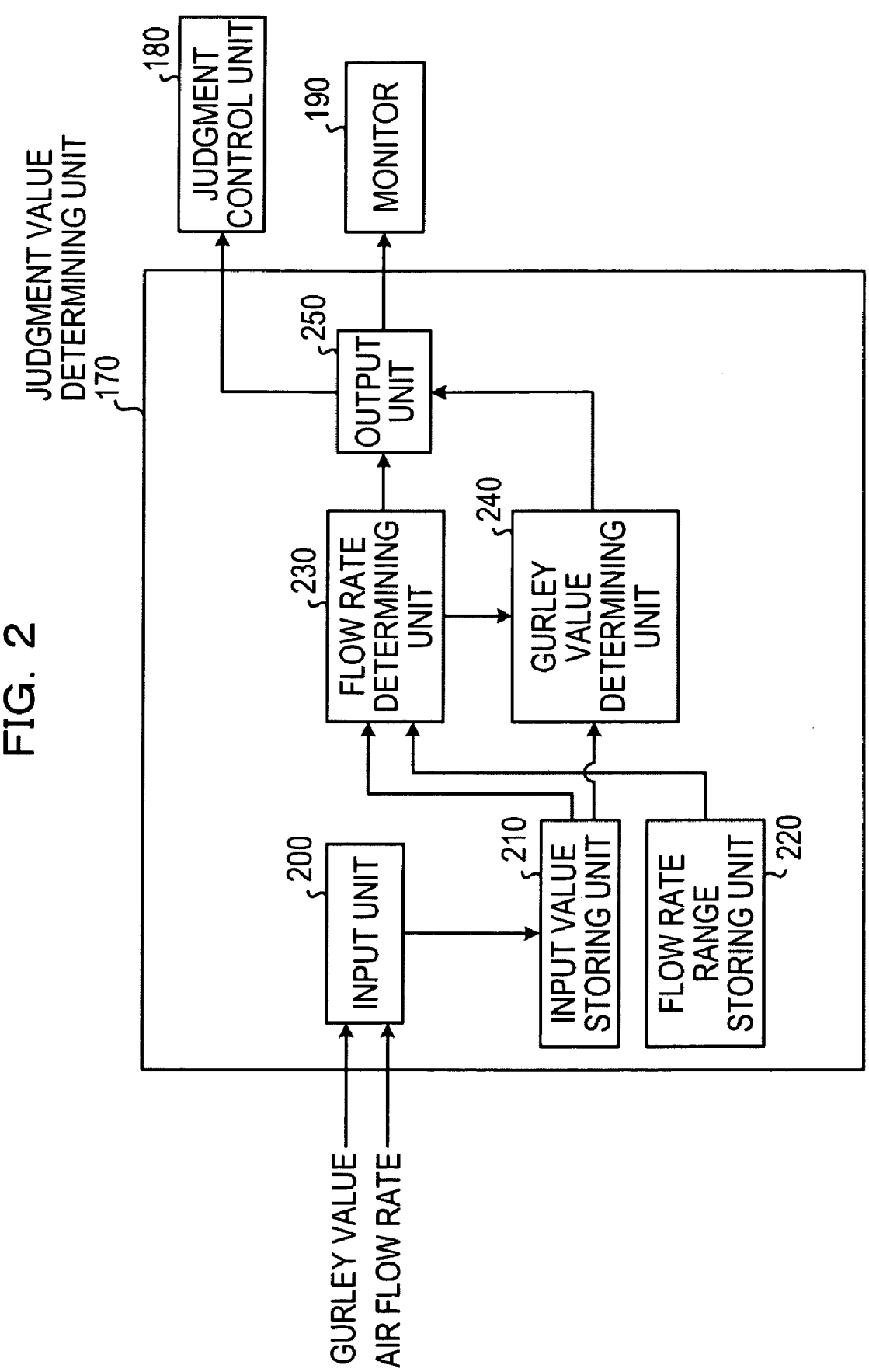

WATERPROOF TESTING DEVICE, WATERPROOF TESTING METHOD, AND WATERPROOF TEST PROGRAM

CROSS-REFERENCE TO RELATED APPLICATIONS

This application claims the benefit of priority from Japanese Patent Application No. 2007-329322 filed on Dec. 20, 2007, which is herein incorporated by reference in its entirety.

FIELD

Embodiments of the present invention relate to a waterproof testing device, a waterproof testing method, and a computer-readable recording medium storing a waterproof testing program. The device, the method, and the computer-readable medium include a technique for testing a product apparatus having a waterproof sheet with pores disposed thereon, for example.

BACKGROUND

Generally, a waterproof sheet is used to waterproof of an acoustic unit for inputting and outputting voices and a breathing unit for balancing pressure. Example of acoustic units, which may be included a mobile phone include a speaker and a microphone. A waterproof test of the waterproof sheet may be performed by taking advantage of a characteristic of permeability indicating how much air passes through the waterproof sheet. That is, the waterproof test is performed by replacing water passing through the waterproof sheet with air.

There is a technique related to a method for measuring permeability based on a flow of air passing through a ventilation material (such as a waterproof sheet, for example) and a pressure difference between the back surface and the front surface of the ventilation material (see Japanese Laid-Open Patent Publication No. 2003-165172 (hereinafter referred to as Patent Document 1)).

SUMMARY

At least one example of an embodiment of the present invention provides a waterproof testing device. The waterproof testing device includes an input unit, a storing unit and a determining unit. The input unit inputs permeability of waterproof components disposed on test objects and an air flow rate that is a volume of gas passing through the waterproof component and the corresponding test object per unit time for each of the test objects. The storing unit stores a data pair including the permeability and the air flow rate of the waterproof component of each test object input by the input unit. The determining unit determines a range of permeability in which no water leakage occurs in the waterproof component based on a range of air flow rate in which no water leakage occurs and the stored permeability and air flow rate.

It is to be understood that both the foregoing summary description and the following detailed description are explanatory as to some example of embodiments of the present invention, and not restrictive of the present invention as claimed.

BRIEF DESCRIPTION OF THE DRAWINGS

Embodiments are illustrated by way of example and not limited by the following figures.

FIG. 2 depicts a judgment value determining unit according to an example of an embodiment of the present invention;

DETAILED DESCRIPTION OF EXAMPLES OF EMBODIMENTS

Figure 1:
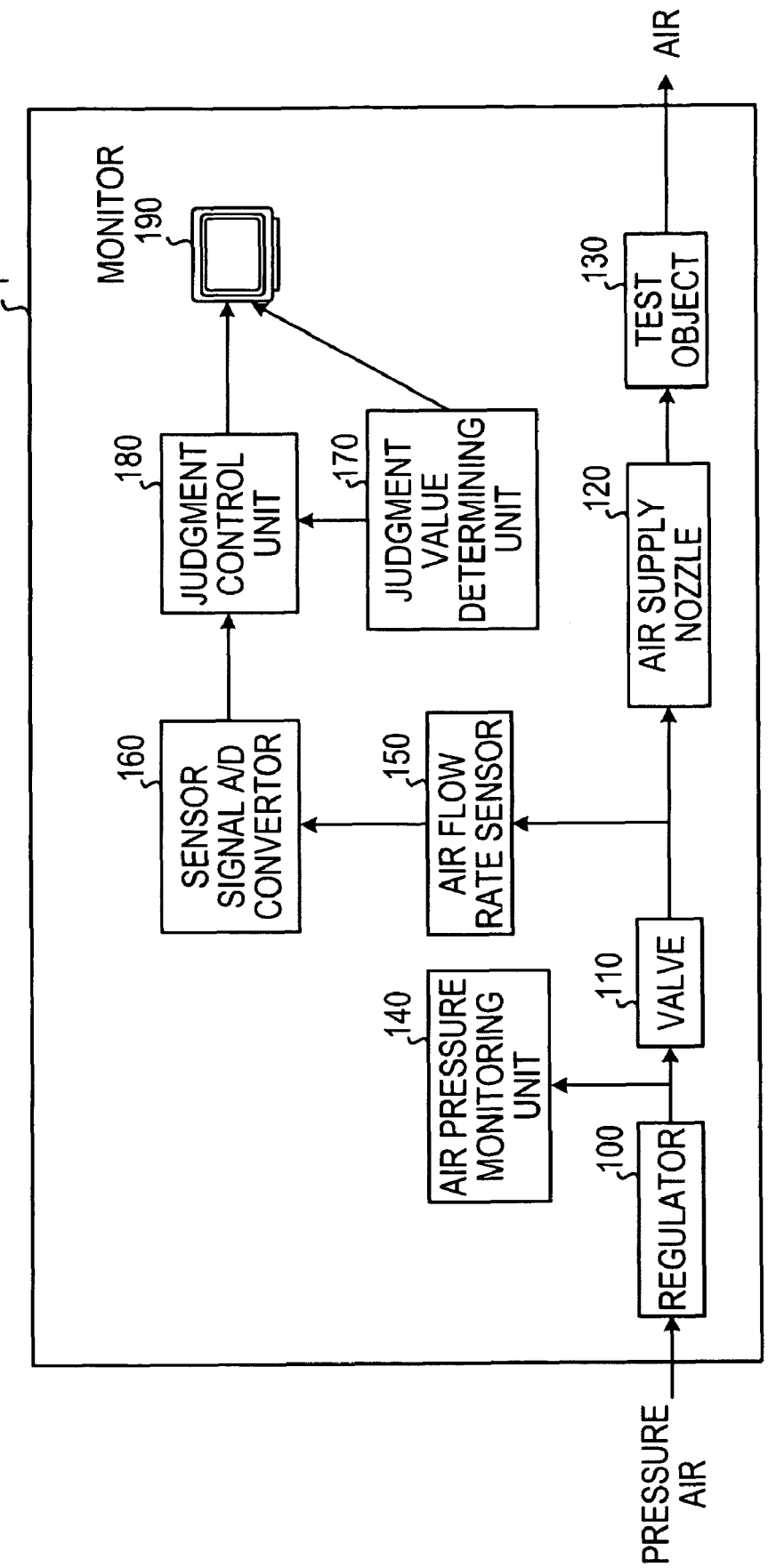
FIG. 1 depicts a waterproof testing device according to an example of an embodiment of the present invention.

In the figures, dimensions and/or proportions may be exaggerated for clarity of illustration. It will also be understood that when an element is referred to as being "connected to" another element, it may be directly connected or indirectly connected, i.e., intervening elements may also be present. Further, it will be understood that when an element is referred to as being "between" two elements, it may be the only element layer between the two elements, or one or more intervening elements may also be present. Like reference numerals refer to like elements throughout.

As part of inventing the present invention, observations were made regarding there being problems with the related method previously referred to in the Description of Related Art subsection. For example, Patent Document 1 describes a related method for measuring the permeability of the ventilation material, rather than a waterproof testing method or technique. That is, the related technique described in the Patent Document 1 is just for efficiently measuring the permeability of the ventilation material, and is not well suited to determining whether or not the ventilation material is suitable for waterproofing devices.

Further, the permeability of the waterproof sheet varies depending on the area being measured of the waterproof sheet. For example, measuring different locations on the waterproof sheet may provide different results in light of the variation. Dispersion of the permeability may occur in a waterproof sheet resulting in components not being sufficiently protected. The related techniques may not address a problem related to inadequate areas of a waterproof sheet causing water leakage. Accordingly, sheets having inadequate areas may not be able to be efficiently excluded based on permeability according to related techniques.

Accordingly, at least one embodiment of the present invention provides a waterproof testing device, a waterproof testing method, and a waterproof testing program for properly performing a waterproof test of a product apparatus with a waterproof sheet disposed thereon even though the waterproof sheet has dispersion characteristics.

Examples of embodiments of the present invention are described below with reference to the figures and provide a waterproof testing device, a waterproof testing method, and a computer-readable medium storing a waterproof testing program that (among other things) address the above noted deficiencies of related techniques and problems noted above.

FIG. 1 depicts a waterproof testing device. As shown in FIG. 1, the waterproof testing device 1 includes a regulator 100, a valve 110, an air supply nozzle 120, a test object 130, an air pressure monitoring unit 140, an air flow rate sensor 150, a sensor signal A/D converter 160, a judgment value determining unit 170, a judgment control unit 180, and a monitor 190.

The regulator 100 inputs air applied with a substantially fixed pressure (hereinafter referred to as "pressurized air") and outputs the pressurized air to the valve 110 while keeping the pressure of the pressurized air substantially fixed. The regulator 100 provides pressurized air to the valve 110 and the air pressure monitoring unit 140.

The valve 110 opens when the pressurized air has a specified pressure and outputs the pressurized air the air supply nozzle 120. The air supply nozzle 120 supplies the pressurized air output by the valve 110 to the test object 130.

The test object 130 may have a waterproof component from a waterproof sheet disposed thereon. For example, the waterproof component is cut from the waterproof sheet and may have a specified shape. If the product apparatus is a mobile phone, the test object 130 may be an acoustic unit (such as a speaker or a microphone, for example) or a breathing unit with a waterproof component disposed thereon. A waterproof component may have pores, which allow air to pass through, but may inhibit or prevent water from passing through. The pores may be provided in order to provide ventilation for the acoustic unit or breathing unit, for example. Pressurized air may flow through the waterproof component of the test object 130 as indicated in FIG. 1.

The air pressure monitoring unit 140 monitors whether or not the air pressure flowing between the regulator 100 and the valve 110 is stable. If the air pressure is not stable, the air pressure monitoring unit 140 notifies that the air pressure is unstable to, for example, an administrator of the waterproof testing device 1 by outputting a warning message to the monitor, sounding a buzzer, blinking a lamp, or the like.

The air flow rate sensor 150 measures the volume of the air flow rate between the valve 110 and the air supply nozzle 120 per unit time (hereinafter referred to as "air flow rate"). When the air supply nozzle 120 supplies the pressurized air output by the valve 110 to the test object 130, the waterproof component disposed on the test object 130 allows the air to pass through. Whether the air passes through the waterproof component easily or not, depends, at least in part, on the size of the pores of the waterproof component. That is, when the pores of the waterproof component are large, a measurement value of the air flow rate sensor 150 is high. Comparatively, when the pores of the waterproof component are small, the measurement value of the air flow rate sensor 150 is small.

The sensor signal A/D converter 160 receives a signal representing the measured air flow rate from the air flow rate sensor 150. The sensor signal A/D converter 160 converts the received signal indicating the air flow rate detected by the air flow rate sensor 150 into a digital signal.

The judgment value determining unit 170 determines an upper limit value and a lower limit value for specifying a range of air flow rate in which no water leakage occurs in the waterproof component disposed on the test object 130. Further, the judgment value determining unit 170 determines a range of permeability in which no water leakage occurs in the waterproof component disposed on the test object 130. Then the judgment value determining unit 170 outputs the determined range of permeability and range of air flow rate to the monitor 190. Further, the judgment value determining unit 170 outputs the determined range of air flow rate to the judgment control unit 180. The judgment value determining unit 170 will be described below in detail.

The judgment value determining unit 170 enables the waterproof testing device 1 to exclude a waterproof component disposed on a test object 130 that does note have a permeability within the range of permeability in which no water leakage occurs in the waterproof component from further testing. After excluding waterproof components that do not have a permeability within the range of permeability in which no water leakage occurs, the waterproof testing device 1 may further perform a waterproof test based on the range of air flow rate in which no water leakage occurs.

After excluding waterproof components disposed on test objects that are not within the determined range of permeability, the waterproof testing device 1 may perform the waterproof test more precisely by determining whether or not the remaining test objects having waterproof components disposed thereon are included between the upper limit value and the lower limit value of gas flow as judged by the judgment value determining unit 170.

Since a measurement result of gas flow (e.g., air flow rate) is obtained by instantly measuring the volume of the air per unit time, the waterproof test may be performed in a relatively short time by performing the waterproof test based on the gas flow rate, which may reduce costs involved in operation of a production line in a factory.

As indicated above, the permeability is an indication of how easily air passes through the waterproof component. The permeability may be represented by a Gurley value (specified in the Japanese Industrial Standards (JIS) P8117).

The judgment control unit 180 performs the waterproof test with respect to a waterproof component disposed on a test object 130, which is within the range of Gurley values determined by the judgment value determining unit 170, by using the range of air flow rate in which no water leakage occurs. That is, the judgment control unit 180 receives an upper limit value and a lower limit value specifying the range of air flow rate, in which no water leakage occurs from the judgment value determining unit 170. The judgment control unit 180 stores the upper limit value and the lower limit value. Then the judgment control unit 180 inputs the digital value showing the air flow rate of the test object with the waterproof component arranged thereon output by the sensor signal A/D convertor 160 to determine whether or not the digital value is within the range of air flow rate in which no water leakage occurs. If the input digital value is within the range of the stored air flow rate, the waterproof component and test object 130 are considered to pass the waterproof test. Alternatively, if the input digital value is not within the range of the stored air flow rate, the waterproof component and test object 130 are considered to fail the waterproof test.

While the waterproof test described above involves measuring air flow rate, a gas other than air may be used in the waterproof testing device 1.

As described above, after excluding waterproof components that are not within a specified range of Gurley values, the waterproof testing device 1 may perform the waterproof test more precisely by determining whether or not the air flow rate of the remaining waterproof components and test objects is included between the upper limit value and the lower limit value in which no water leakage occurs in order to determine pass or fail of the waterproof test.

A connecting component may connect the waterproof component and the test object 130. For example, when the waterproof component is disposed on the test object 130, the waterproof testing device 1 may perform the waterproof test even in the state where the waterproof component is damaged or where dust enters into the connecting component between the waterproof component and the test object 130.

The waterproof test may be performed on different test objects and with different waterproof components disposed on the test object 130. Further, different types of test objects may be used. However, if the different waterproof components or different types of test objects are tested, the judgment value determining unit 170 determines the upper limit value and the lower limit value for specifying the range of air flow rate in which no water leakage occurs, and outputs the values to the judgment control unit 180.

FIG. 2 depicts a judgment value determining unit. In FIG. 2, the judgment value determining unit 170 includes an input unit 200, an input value storing unit 210, a flow rate range storing unit 220, a flow determining unit 230, a Gurley value determining unit 240, and an output unit 250.

The input unit 200 inputs a plurality of the Gurley values formed using the waterproof component and the air flow rate for each test object. At this time, a test object is referred to as a component in the state where the waterproof sheet used for waterproofing the product apparatus is disposed on the component of the product apparatus.

The input unit 200 may receive a measurement result automatically from the measuring device of the Gurley value (not shown in FIG. 2), and the measuring device of the air flow rate (not shown in FIG. 2), and may receive the already-measured measurement result that is input manually.

The input value storing unit 210 includes, for example, a memory and a disc device, and stores as a pair, for example, the Gurley value and the air flow rate of each test object input by the input unit 200.

The flow rate range storing unit 220 stores the range of air flow rate in which no water leakage occurs in the waterproof component used for the product apparatus.

The flow determining unit 230 determines the lower limit value and the upper limit value in which no water leakage occurs in the waterproof component and the test object. For example, the flow determining unit 230 detects the lower limit value of air flow rate stored by the input value storing unit 210, and then adds the range of air flow rate, in which no water leakage occurs, stored by the flow rate range storing unit 220 to the lower limit value to determine the upper limit value of the air flow rate.

While the waterproof testing device 1 considers the size of one or more pores formed in a waterproof component, the waterproof testing device 1 determines the upper limit value of gas flow by using the range of gas flow, in which no water leakage occurs in the waterproof component. The range of gas flow is independent from the size of the waterproof component. Therefore, the waterproof testing device 1 may determine the upper limit value of gas flow without regardless of the size of the waterproof component to be disposed on the test object.

The Gurley value determining unit 240 determines the range of Gurley value in which no water leakage occurs in the waterproof component based on the range of air flow rate in which no water leakage occurs in the waterproof component and the Gurley value and the air flow rate stored by the input value storing unit 210. Specifically, for example, the Gurley value determining unit 240 obtains a correlation between the Gurley value and the air flow rate based on the data (e.g., a data pair including the Gurley value and the air flow rate for each test object) stored by the input value storing unit 210, determines the lower limit value of the Gurley value based on the obtained correlation and the upper limit value of the air flow rate determined by the flow determining unit 230, and determines the upper limit value of the range of Gurley values based on the obtained correlation and the lower limit value of the air flow rate determined by the flow determining unit 230.

The Gurley value determining unit 240 allows the waterproof testing device 1 to more precisely indicate a waterproof component disposed on a test object may cause water leakage even though the permeability of the waterproof component has dispersion by determining the range of Gurley value in which no water leakage occurs in the waterproof component based on the range of gas flow in which no water leakage occurs in the waterproof component, the stored Gurley value, and the stored air flow rate.

The output unit 250 outputs the lower limit value and the upper limit value of the air flow rate determined by the flow determining unit 230 to the monitor 190, and outputs the lower limit value and the upper limit value determined by the Gurley value determining unit 240 to the monitor 190. Further, the output unit 250 outputs, to the judge control unit 180, the lower limit value and the upper limit value of the air flow rate determined by the flow determining unit 230.

Figure 3A:
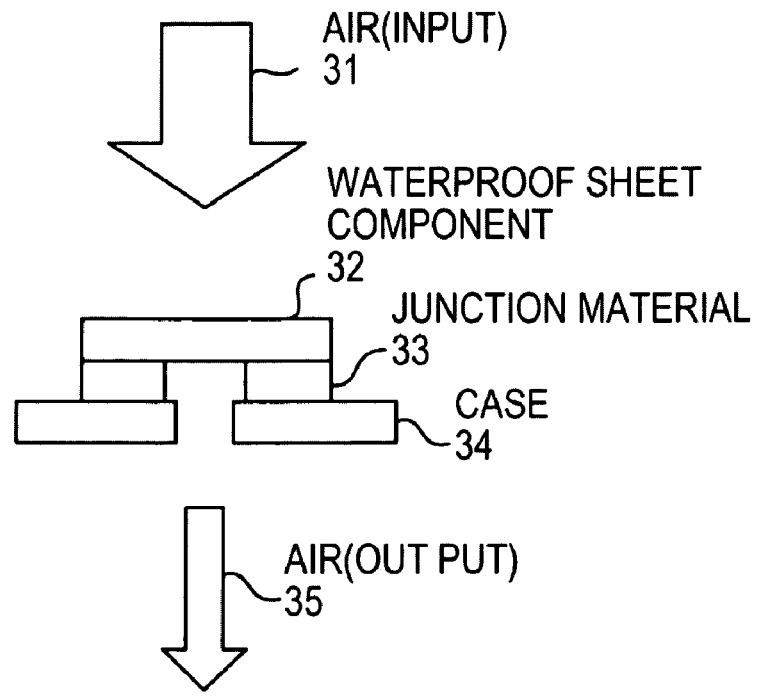
FIG. 3A depicts an air flow rate of the case when no water leakage occurs according to an example of an embodiment of the present invention.
Figure 3B:
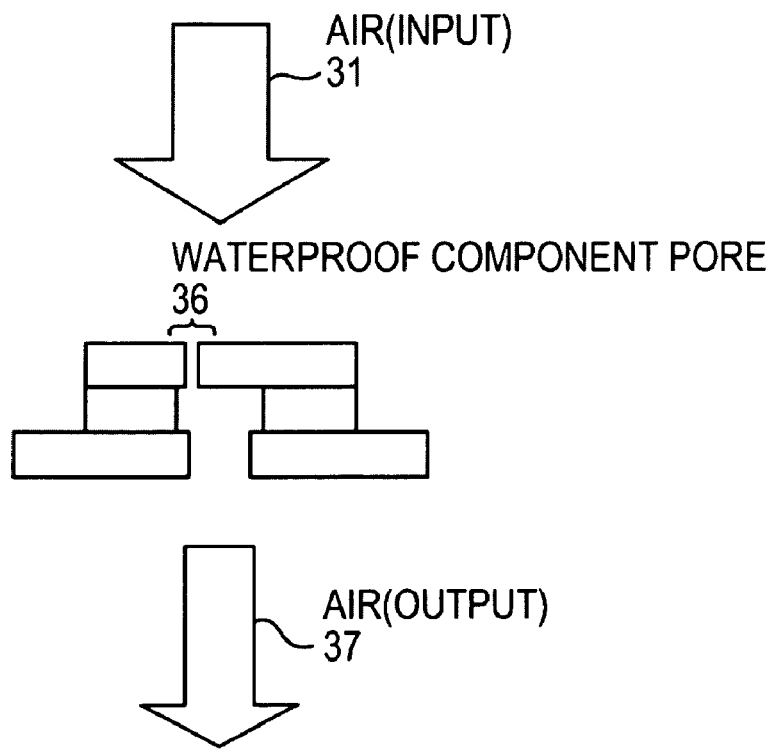
FIG. 3B depicts an air flow rate of the case when water leakage occurs according to an example of an embodiment of the present invention.

Next, with reference to FIG. 3A and FIG. 3B, a change of the air flow rate passing through the waterproof component disposed on a test object is described with respect to an example in which no water leakage occurs and an example in which water leakage does occur.

FIG. 3A depicts an air flow rate of an example in which no water leakage occurs. In FIG. 3A, the test object 130 includes a case 34, a junction material 33, and a waterproof sheet component 32 and an air flow rate of the air 35 is shown. The air flow rate of the air 35 passing through the waterproof component 32 in response to the applied pressurized air 31 to the waterproof sheet component 32 is indicated by the width of the arrow.

The junction material 33 joins the case 34 and the waterproof sheet component 32. The case 34 is an outside of the test object 130, which may be exposed to air. In FIG. 3A, each of the case 34 and the junction material 33 has a gap through which air passes. This is because, for example, if the test object 130 is a microphone, the gap is for inputting voices, and if the test object 130 is a speaker, the gap is for outputting voices. Similarly, if the test object 130 is a breathing unit, the gap is for ventilation. Further, the waterproof component 32 is attached to the test object 130 by using the junction material 33 to reduce the likelihood of water leakage from occurring from the gap of the case 34 into the inside of the product apparatus.

In this manner, even though each of the case 34 and the junction material 33 has a gap through which air passes, respectively, no water leakage occurs if the waterproof sheet component 32 has no pores other than the pores for ventilation shown in the case 34 and the junction material 33.

FIG. 3B depicts the air flow rate in an example when water leakage occurs. FIG. 3B depicts that the test object 130 including the case 34 and the waterproof component 36, which has a pore, has pressurized air 31 applied thereto. The air flow rate of air 37 passing through the waterproof component 36 is indicated by the width of the arrow.

When the pressurized air 31 having the same pressure is applied to the waterproof component 36, which has a pore, the air flow rate that is the volume of the air passing through the waterproof component 36 in a specified period of time is larger than that of the waterproof sheet 32 having no pores. In general, the larger the pore of the waterproof sheet, the greater the air flow rate through the waterproof sheet.

If each of the case 34 and the junction material 33 has a gap through which the air passes, respectively, water leakage is related to the size of the waterproof sheet component pore. Therefore, it is possible to determine the range of air flow rate in which no water leakage occurs depending on a difference of the air flow rate caused by the size of the pore of the waterproof sheet component.

Figure 4:
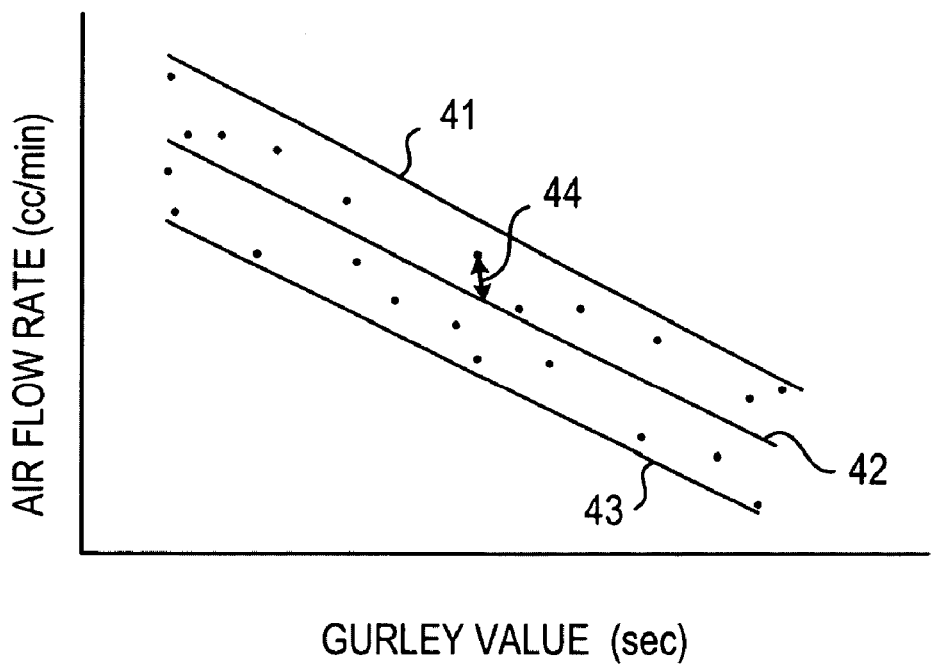
FIG. 4 depicts correlation between a Gurley value and an air flow rate according to an example of an embodiment of the present invention.

FIG. 4 depicts correlation of air flow rate between the Gurley value and the air flow rate input by the input unit 200. As shown in FIG. 4, the X coordinate indicates a Gurley value (second), and the Y coordinate indicates an air flow rate (cc/minute).

The graph in FIG. 4 indicates the Gurley value and the air flow rate input by the input unit 200 for each of a plurality of test objects with the waterproof sheet disposed thereon. As the Gurley value increases, the air flow rate decreases. Thus, the correlation is provided between the Gurley and the air flow rate. The Gurley value determining unit 240 obtains a regression line based on the input Gurley value and air flow rate, and then obtains primary straight lines of the upper limit and the lower limit of the Gurley value and the air flow rate.

For example, first, the input unit 200 stores, in the input value storing unit 210 pairs of the Gurley value and air flow rate, which are input for each of a plurality of components which are test objects having waterproof sheets disposed thereon. Next, the input unit 200 stores the Gurley value and the air flow rate in the input value storing unit 210 in a pair, which are input for each test object by using a waterproof component including the upper limit value of the Gurley value and the waterproof sheet including the lower limit value of the Gurley value of the waterproof sheets.

Next, the Gurley value determining unit 240 obtains a regression line 42 based on the input Gurley value and air flow rate for each of a plurality of test objects. For example, the regression line 42 can be obtained by linear analysis. Next, the Gurley value determining unit 240 obtains primary straight lines of the upper limit and the lower limit including the Gurley value and the air flow rate having the correlation. That is, the Gurley value determining unit 240 obtains a distance 44 between the data paired with the Gurley value and the air flow rate stored by the input value storing unit 210, determines that the line moved in parallel toward the plus direction of the Y coordinate to the regression line 42 by the maximum distance is a primary straight line 41, and determines that the line moved in parallel toward the minus direction of the Y coordinate to the regression line 42 by the maximum distance is a first line 43. Before the primary straight lines of the upper limit and the lower limit are obtained, it is possible to obtain a more accurate primary straight line by obtaining and removing an outlier that is the data separated from the regression line by more than a specified value in FIG. 4.

The waterproof components disposed on the test object 130 having various functions and types having different areas. Thus, the air flow rates that are the volumes of the air per unit time are different. However, in the description below, the test object 130 is assumed to be the same type of component having the same area of the waterproof component disposed on the test object 130.

Figure 5:
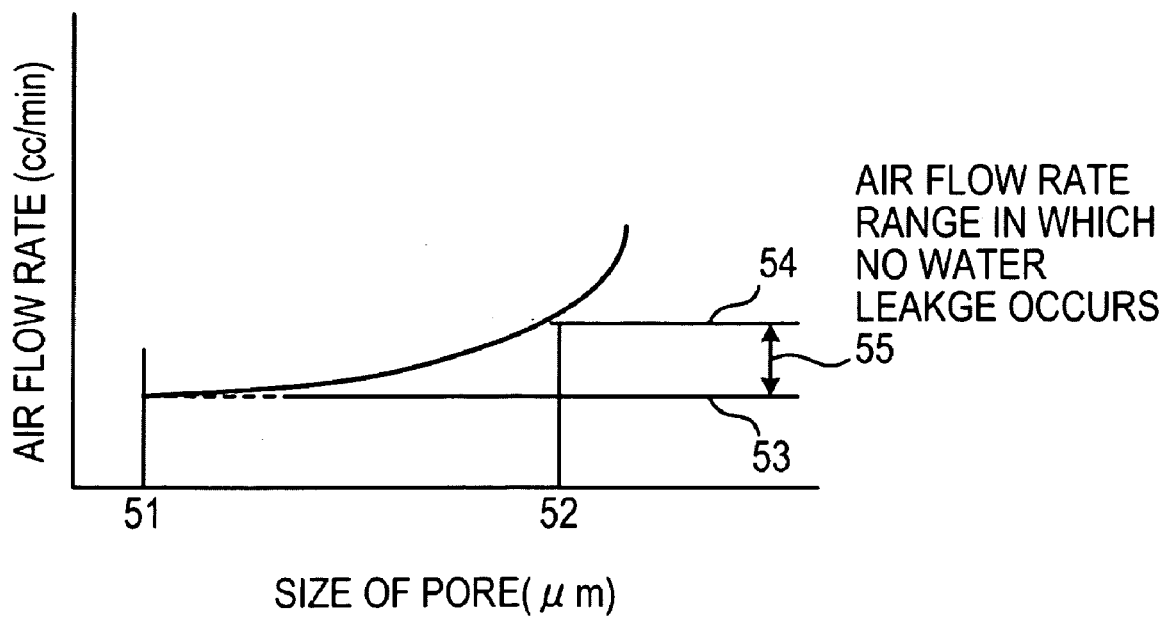
FIG. 5 depicts a range of the air flow rate in which no water leakage occurs according to an example of an embodiment of the present invention.

FIG. 5 depicts a range of air flow rate in which no water leakage occurs that may be stored in the flow rate range storing unit 220. As shown in FIG. 5, the X coordinate indicates a size of the pore of a waterproof component (μm). The Y coordinate indicates an air flow rate (cc/minute). The pore of the waterproof sheet is expanded step by step, and the air flow rate that is measured each time is shown. For example, the pore of the waterproof components may be incrementally expanded. When the size of the pore of the waterproof component is incrementally expanded, the increments should be as small as possible, 1 μm, for example.

The waterproof sheet has pores allowing air to pass through, but not water. Therefore, the air flow rate of the case when the size of the pore of a waterproof component is small corresponds to an air flow rate 53 of the state where the waterproof sheet has no pores. However, when the size of the pore of a waterproof component is incrementally expanded, the air flow rate increases little by little. A size 52 becomes the limit of an air flow rate 54 in which no water leakage occurs. Water leakage occurs when the air flow rate becomes greater than the size 52. Accordingly, the range between the air flow rate 53 of the state where the waterproof sheet has no pores and the limit of the air flow rate 54 in which no water leakage occurs becomes an air flow rate range 55 in which no water leakage occurs. The air flow rate 54 in which no water leakage occurs is obtained, for example, by testing whether or not a specified waterproof performance (e.g., a waterproof performance at a depth of one meter) is maintained when the air flow rate of the waterproof sheet having the pores is measured.

Since the air flow rate range in which no water leakage occurs depends on the size of the pore in which water leakage occurs, the air flow rate range does not change even if the size of the waterproof sheet is changed.

Figure 6:
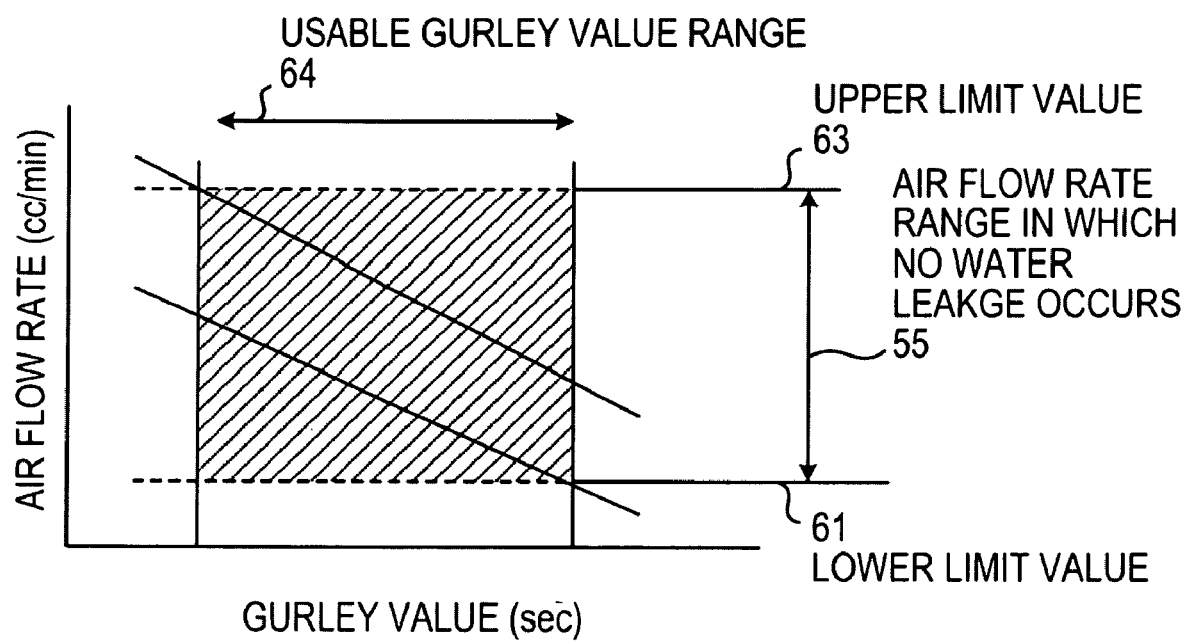
FIG. 6 depicts a passing range of a waterproof test.

FIG. 6 depicts a passing range of the waterproof test determined by the Gurley value determining unit 240. As shown in FIG. 6, the X coordinate indicates a Gurley value (second), and the Y coordinate indicates an air flow rate (cc/minute). The range of Gurley value in which no water leakage occurs in the waterproof sheet component is determined based on the air flow rate and Gurley value stored in the input value storing unit 210 and the air flow rate range in which no water leakage occurs stored in the flow rate range storing unit 220.

First, the flow determining unit 230 determines a lower limit value 61 of the air flow rate. For example, the lower limit value 61 of the air flow rate is assumed to be the lower limit value of the air flow rate of the test object stored in the input value storing unit 210. Then, the flow determining unit 230 adds the air flow rate range 55 in which no water leakage occurs to the lower limit value 61 of the air flow rate to determine an upper limit value 63 of the air flow rate. After determining the upper limit value 63 of the air flow rate, the flow determining unit 230 may reduce the air flow rate range 55 in which no water leakage occurs to determine the lower limit value 61 of the air flow rate.

Figure 7:
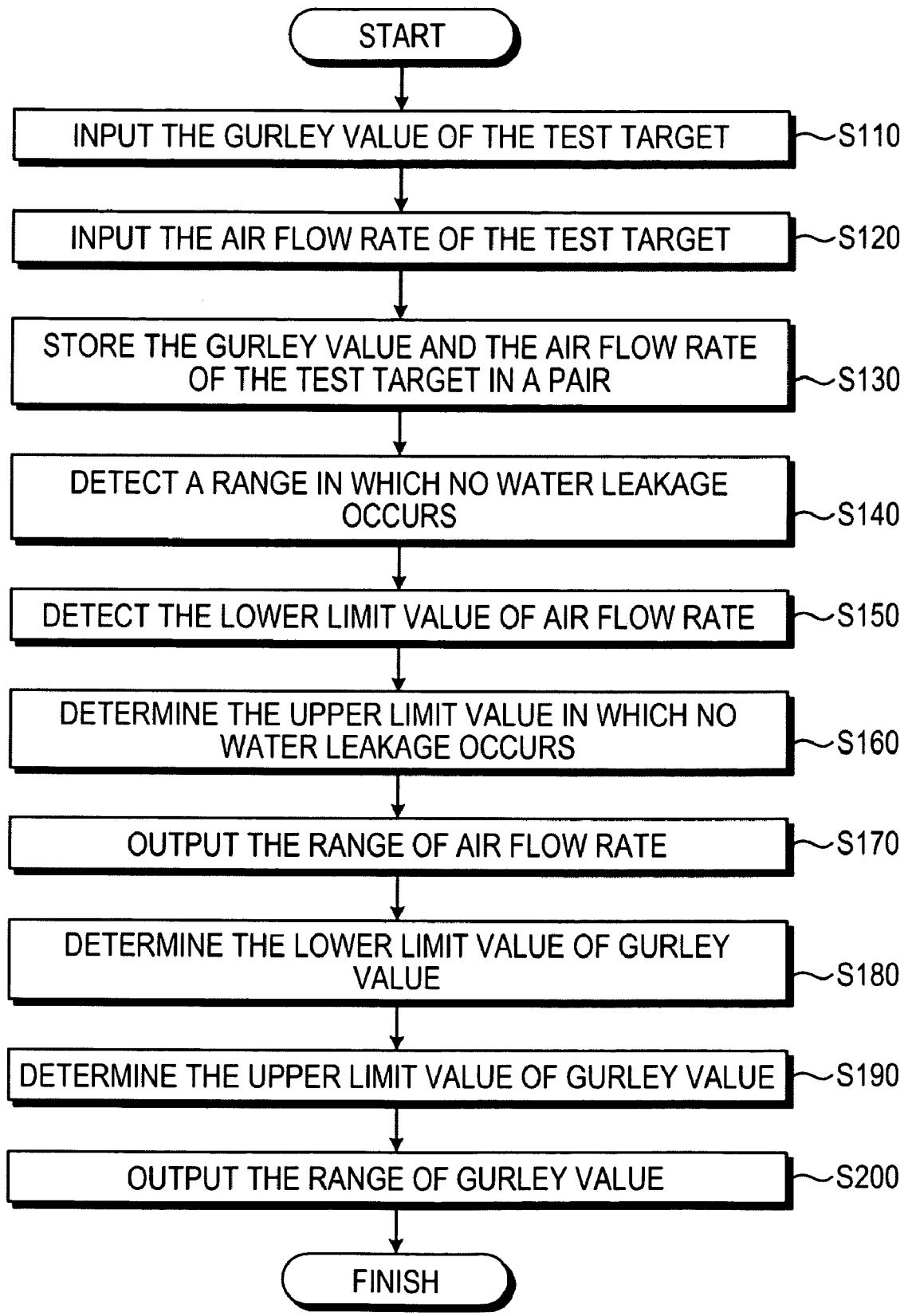
FIG. 7 depicts a processing procedure of the judgment value determining unit.

Next, the Gurley value determining unit 240 determines that the Gurley value at an intersection corresponding to a smaller Gurley value of the intersections of the above described primary straight line 41 of the upper limit, the primary straight line 43 of the lower limit, and the lower limit value 61 of the air flow rate (hereinafter referred to as "the minimum value of intersection") is the upper limit value of the Gurley value. Then, the Gurley value determining unit 240 determines that the Gurley value at an intersection corresponding to the larger Gurley value of the intersections of the primary straight line 41 of the upper limit, the primary straight line 43 of the lower limit, and the upper limit 63 of the air flow rate (hereinafter referred to as "the maximum value of intersection") is the lower value of the Gurley value. The difference between the upper limit value and lower limit value of the Gurley value determined as described above is the range of Gurley value in which no water leakage occurs in the waterproof sheet component and becomes a Gurley value range 64 that can be used as the passing range of the waterproof test. FIG. 7 is a flowchart showing a processing procedure of a judgment value determining unit.

The lower limit value 61 of the air flow rate increases as the area of the waterproof component increases. Accordingly, a usable Gurley value range 64 differs depending on the area of the waterproof component. Therefore, the usable Gurley value range 64 should be determined for each of the different components which are the test objects and that may have different sized waterproof components arranged thereon.

By determining the range of the usable Gurley value as the passing range of the waterproof test of the test object with the waterproof test component mounted thereon, the waterproof testing device 1 may exclude a waterproof component causing water leakage even though the Gurley value of the waterproof sheet has dispersion.

Next, description of a processing procedure of the judgment value determining unit 170 is provided with reference to FIG. 7 and FIG. 2. FIG. 7 is a flowchart depicting the processing procedure of the judgment value determining unit.

First, the input unit 200 inputs the Gurley value for each test object (S110). Further, the input unit 200 inputs the air flow rate for each test object (S120). Then the input unit 200 gives the input Gurley value and air flow rate for each test object to the input value storing unit 210. The input unit 200 receives, for example, the Gurley value and the air flow rate of the test object input by a person in charge of the test. The person in charge of the test refers to a screen on which the Gurley value and the air flow rate are displayed on the monitor 190, which is connected to the judgment value determining unit 170.

The input value storing unit 210 including, for example, a memory or a magnetic disk device stores, as a pair, the Gurley value and the air flow rate for each test object input by the input unit 200 (S130). That is, the input value storing unit 210 receives the Gurley value and the air flow rate given from the input unit 200 and stores the Gurley value and the air flow rate as an element of a record.

If the test objects are not all the same type, the input value storing unit 210 can add identification information identifying the component when the Gurley value and the air flow rate of the test object are stored in a pair.

Next, the flow determining unit 230 detects the range of air flow rate, in which no water leakage occurs, stored by the flow rate range storing unit 220 (S140). The pore of the waterproof sheet is expanded incrementally, and the air flow rate measured during each increment until reaching the limit of the air flow rate in which no water leakage occurs. At this time, the range of air flow rate in which no water leakage occurs in the waterproof sheet is determined by the range between the air flow rate of the state where the waterproof sheet has no pores and the limit of the air flow rate in which no water leakage occurs.

Then the flow determining unit 230 detects the lower limit value of the air flow rate stored by the input value storing unit 210 (S150).

The flow determining unit 230 may detect the lower limit value for each waterproof component of the test object when the test objects are not limited to the same type. That is, the flow determining unit 230 may specify identification information to detect the lower limit value.

Then the flow determining unit 230 determines the upper limit value of the air flow rate in which no water leakage occurs (S160). That is, the flow determining unit 230 adds the detected range of the air flow rate in which no water leakage occurs to the detected lower limit value of the air flow rate to determine the upper limit value of the air flow rate. Then the flow determining unit 230 provides the lower limit value and upper limit value of air flow rate to the Gurley value determining unit 240.

Then the flow determining unit 230 outputs the range of air flow rate (S170). That is, the flow determining unit 230 outputs the lower limit of air flow rate and the upper limit value of the air flow rate to the monitor 190, and then to the judgment control unit 180.

Next, the Gurley value determining unit 240 determines a lower limit value of the Gurley value based on the Gurley value and the air flow rate for each test object stored by the input value storing unit 210 and the range of air flow rate determined by the flow determining unit 230 (S180). Specifically, the Gurley value determining unit 240 calculates a regression line 42 based on the data included in a pair of the Gurley value and the air flow rate for each test object stored by the input value storing unit 210. Then the Gurley value determining unit 240 calculates the maximum value of the distance 44 between the calculated regression line 44 and the data of each test object. Next, the Gurley value determining unit 240 calculates an upper limit primary straight line 41 that is a line moved to the calculated maximum value regression line in parallel in the upper part. The Gurley value determining unit also calculates a lower limit primary straight line 43 that is a line moved to the calculated maximum value regression line in parallel in the lower part. Further, the Gurley value determining unit 240 determines that the maximum value of the intersection of the upper limit primary straight line 41, the lower limit primary straight line 43, the upper limit value of the air flow rate determined by the flow determining unit 230 is the lower limit value of the range of Gurley value.

Then the Gurley value determining unit 240 determines the upper limit value of the Gurley value (S190). Specifically, the Gurley value determining unit 240 determines that the minimum value of the intersection of the upper limit primary straight line 41 and the lower limit primary straight line 43, and the lower limit value of the air flow rate determined by the flow determining unit 230 as the upper limit value of the range of Gurley value.

If the test object is not limited to the component of the same type, the Gurley value determining unit 240 determines the upper limit value and lower limit value of Gurley value for each component of the test object. That is, the Gurley value determining unit 240 may specify the identification information to detect the upper limit value and lower limit value of Gurley value.

The Gurley value determining unit 240 outputs the lower limit value and upper limit value of Gurley value for specifying the range of the determined Gurley value (S200).

As described above, according to the present embodiment, the waterproof testing device 1 inputs the Gurley value and the air flow rate for each test object with the waterproof component disposed thereon, stores the Gurley value and the air flow rate for each input test object in a pair, and determines the range of Gurley value in which no water leakage occurs in the waterproof sheet component based on the range of air flow rate in which no water leakage occurs in the waterproof sheet component stored in advance and the stored Gurley value and the air flow rate for each test object.

Therefore, the waterproof testing device 1 may determine the range of Gurley value that can be used as the passing range of the waterproof test of the test object with the waterproof sheet component disposed thereon, and can appropriately exclude the waterproof component in which water leakage occurs in the test objects with the waterproof components disposed thereon based on the Gurley value.

Accordingly, the waterproof testing device, the waterproof testing method, and the waterproof testing program of the present embodiment can appropriately perform the waterproof test of the product apparatus with the waterproof sheet disposed thereon.

As described above, the waterproof testing device, the waterproof testing method, and the computer-readable recording medium storing waterproof testing program described herein are useful for testing a product apparatus with a waterproof component particularly suitable for a waterproof test of a mobile phone.

The examples of embodiments of the present invention described above are not intended to limit the disclosed waterproof testing device, waterproof testing method, and computer-readable medium including waterproof testing program. Although examples of embodiments have been described in detail above, it should be understood that the various changes, substitutions, and alterations could be made hereto without departing from the spirit and scope thereof.

At least one embodiment of the present invention may also be embodied as computer readable data including executable instructions that are recorded on a computer readable recording medium. The computer readable recording medium is any data storage device that can store the data, including the executable instructions, and which can be read by a computer system so as to provide the computer system with the executable instructions included in the recorded data for execution. Examples of the computer readable recording medium include read-only memory (ROM), random-access memory (RAM), CD-ROMs, magnetic tapes, floppy disks, and optical data storage devices. The computer readable recording medium may also be distributed over network coupled computer systems so that the computer readable code is stored and executed in a distributed fashion.

Examples of embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made therein without departing from the spirit and scope of the present invention as set forth in the claims.

The invention claimed is:

1. A waterproof testing device comprising:
   a storing unit to store a data pair including permeability of a waterproof component and an air flow rate of the waterproof component, the air flow rate being a volume of gas passing through the waterproof component per unit time;
   a flow determining unit to add a range of air flow rate in which no water leakage occurs to a flow lower limit value in order to determine a flow upper limit value that is an upper limit value of the air flow rate, the flow lower limit value is a lower limit value of the stored air flow rate; and
   a determining unit to determine a range of permeability in which no water leakage occurs in the waterproof component based on the flow lower limit value, the flow upper limit value, and the stored permeability and air flow rate.

2. The waterproof testing device according to claim 1, further comprising:
   a measuring unit to measure an air flow rate passing through a test object having the waterproof component disposed thereon that is within the determined range of permeability; and
   a judgment unit to judge whether or not the measured air flow rate is between the flow lower limit value and the flow upper limit value.

3. A waterproof testing method that tests waterproof performance of a waterproof component, the method comprising:
   accessing a data pair including permeability of a waterproof component and an air flow rate of the waterproof component, the air flow rate being a volume of gas passing through the waterproof component per unit time;
   adding a range of air flow rate in which no water leakage occurs to a flow lower limit value in order to determine a flow upper limit value that is an upper limit value of the air flow rate, the flow lower limit value is a lower limit value of the stored air flow rate; and
   determining, by a determining unit, a range of permeability in which no water leakage occurs in the waterproof component based on the flow lower limit value, the flow upper limit value, and the stored permeability and air flow rate.

4. The waterproof testing method according to claim 3, further comprising:
   measuring an air flow rate passing through the test object with the waterproof component disposed thereon that is within the determined range of permeability; and
   judging whether or not the measured air flow rate is included between the flow lower limit value and the flow upper limit value.

5. A non-transitory computer readable recording medium storing a waterproof testing program for causing a computer processor to perform a method, the method comprising:
   storing a data pair including permeability of a waterproof component and an air flow rate of the waterproof component, the air flow rate being a volume of gas passing through the waterproof component per unit time;
   adding a range of air flow rate in which no water leakage occurs to a flow lower limit value in order to determine a flow upper limit value that is an upper limit value of the air flow rate, the flow lower limit value is a lower limit value of the stored air flow rate; and
   determining a range of permeability in which no water leakage occurs in the waterproof component based on the flow lower limit value, the flow upper limit value and the stored permeability and air flow rate.

6. The non-transitory computer readable recording medium according to claim 5, wherein the method further comprises:
   measuring an air flow rate passing through a test object with the waterproof component disposed thereon that is within the determined range of permeability; and
   judging whether or not the measured air flow rate is included between the flow lower limit value and the flow upper limit value.

7. The waterproof testing method according to claim 3, wherein
   the storing stores the data pair in a storing unit, and the adding and determining are implemented by a computer processor.

8. A waterproof testing device comprising:
   a storing unit to store a data pair including permeability of a waterproof component and an air flow rate of the waterproof component, the air flow rate being a volume of gas passing through the waterproof component per unit time;
   a flow determining unit to reduce a range of air flow rate in which no water leakage occurs from a flow upper limit value in order to determine a flow lower limit value that is a lower limit value of the air flow rate, the flow upper limit value is an upper limit value of the stored air flow rate; and
   a determining unit to determine a range of permeability in which no water leakage occurs in the waterproof component based on the flow lower limit value, the flow upper limit value, and the stored permeability and air flow rate.

* * * * *